(12) United States Patent
Nayet et al.

(10) Patent No.: US 8,052,726 B2
(45) Date of Patent: Nov. 8, 2011

(54) ILIO-SACRAL CONNECTOR SYSTEM AND METHOD

(75) Inventors: Jerome Nayet, Saint Genis Pouilly (FR); Stephan Chojnicki, Aubonne (CH); Lofti Miladi, Bourg la Reine (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 373 days.

(21) Appl. No.: 12/335,708

(22) Filed: Dec. 16, 2008

(65) Prior Publication Data

US 2009/0287254 A1 Nov. 19, 2009

(30) Foreign Application Priority Data

May 13, 2008 (FR) ..................................... 08 53088

(51) Int. Cl.
*A61B 17/70* (2006.01)
(52) U.S. Cl. ........ 606/278; 606/250; 606/260; 606/264; 606/301; 606/304; 606/305; 606/308
(58) Field of Classification Search .......... 606/264–279, 606/300–321, 246–253, 259, 260; 623/17.11–17.16
See application file for complete search history.

(56) References Cited

U.S. PATENT DOCUMENTS

| | | | |
|---|---|---|---|
| 4,773,402 A | 9/1988 | Asher et al. | |
| 5,024,213 A | 6/1991 | Asher et al. | |
| 5,133,717 A | 7/1992 | Chopin | |
| 5,147,360 A | 9/1992 | Dubousset | |
| 5,437,669 A | 8/1995 | Yuan et al. | |
| 5,643,264 A | 7/1997 | Sherman et al. | |
| 5,693,053 A | 12/1997 | Estes | |
| 5,814,046 A | 9/1998 | Hopf | |
| 5,928,233 A | 7/1999 | Apfelbaum et al. | |
| 6,015,409 A | 1/2000 | Jackson | |
| 6,080,156 A | 6/2000 | Asher et al. | |
| 6,520,990 B1 | 2/2003 | Ray | |
| 2006/0106382 A1 | 5/2006 | Gournay et al. | |
| 2008/0306548 A1* | 12/2008 | Cain et al. | 606/264 |

FOREIGN PATENT DOCUMENTS

EP 0841876 B1 7/2002
WO WO9523559 9/1995

* cited by examiner

*Primary Examiner* — Eduardo C Robert
*Assistant Examiner* — Christina Negrelli

(57) ABSTRACT

A system and method for anchoring a connector to a bony portion of a spinal column is provided. The connector is engaged to the spinal column with an anchor. The connector receives an elongate connecting element that extends along two or more vertebrae of the spinal column. The connector includes an eyelet portion that houses a retaining member through which the anchor extends. The retaining member allows movement of the connector relative to the anchor prior to engagement of the connecting element to the connector. When the connecting element is engaged to the connector, the connector is fixed relative to the anchor and the retaining member.

20 Claims, 3 Drawing Sheets

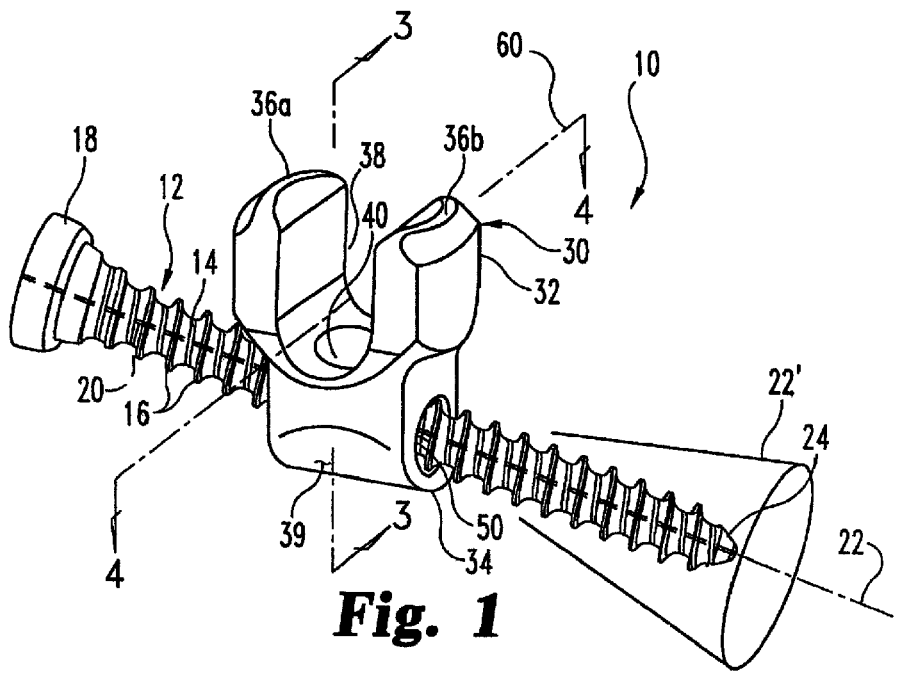
Fig. 1
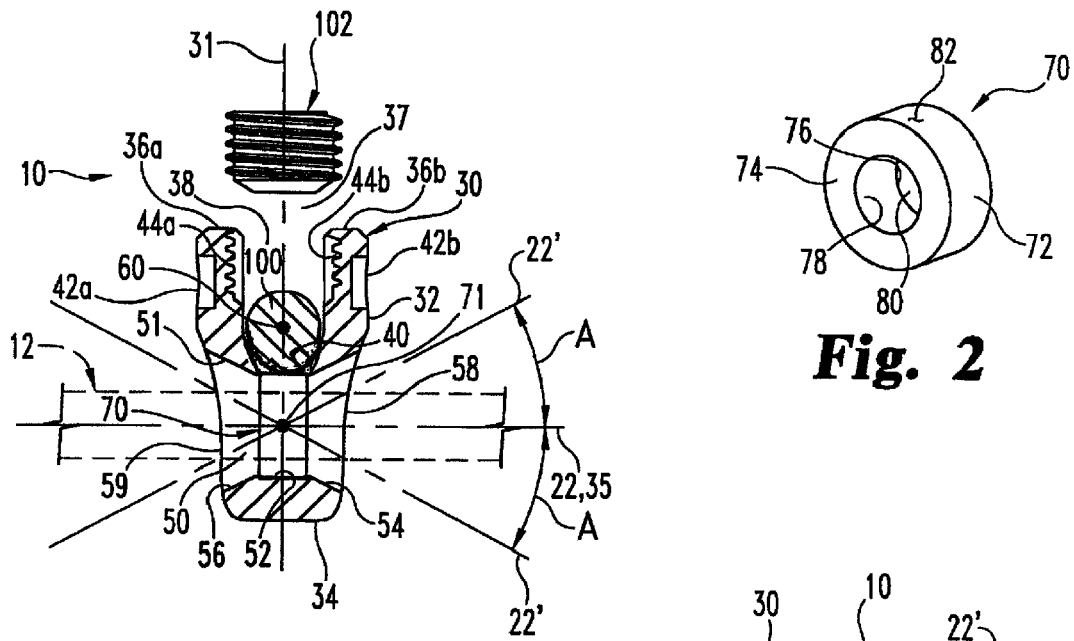
Fig. 3     Fig. 2
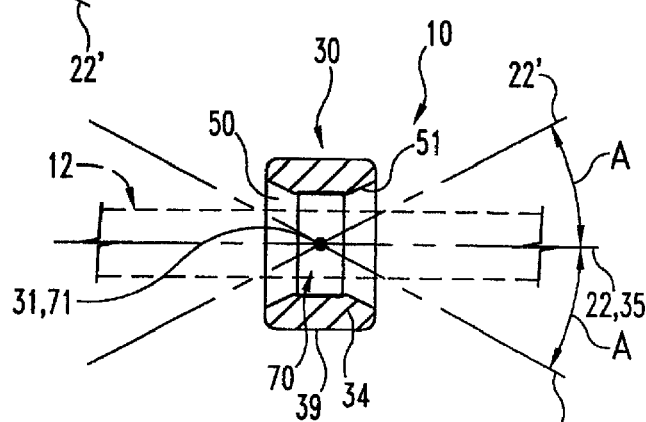
Fig. 4

ILIO-SACRAL CONNECTOR SYSTEM AND METHOD

BACKGROUND

Connectors for rods and other connecting elements along the spinal column can be secured to the bony portions of the spinal column to maintain a desired position or orientation of the connecting element relative to the bony portion in a fixed or dynamic relationship. Anchors such as bone screws can be used to secure the connecting elements to the spinal column. However, over time the anchors may move or backout from their inserted position as a result of forces applied to the anchor due to motion of the bony portions. The anchor movement may cause the anchor to impinge on tissue adjacent its implantation location and less effectively maintain the position of the connecting element relative to the spinal column. Accordingly, systems and methods which reduce or prevent the anchor loosening or backing out from its implanted position would be desirable.

SUMMARY

A system for anchoring a connector to a bony portion of a spinal column is provided. The system includes a connector that is engaged to the spinal column with an anchor. The connector receives an elongate connecting element that extends along two or more vertebrae of the spinal column. The connector includes an eyelet portion that houses a retaining member through which the anchor extends. The retaining member allows movement of the connector relative to the anchor prior to securing the connecting element to the connector. When the connecting element is secured to the connector, the connecting element compresses the retaining member through the connector to secure the retaining member to the anchor and fix the anchor and connector in position relative to another.

In another aspect, a spinal connector system includes a connector with a saddle portion and an eyelet portion depending from the saddle portion to form a monolithic connector body. The saddle portion defines a passage for receiving an elongated connecting element therethrough along a first axis and the eyelet portion includes a receptacle. The receptacle houses a retaining member therein that includes a through-bore extending therethrough along a second axis and a center through which the second axis extends. The connector system also includes an elongated anchor including a shaft positioned through the through-bore along the second axis. The anchor and the retaining member include a first orientation in the eyelet portion where the second axis is orthogonal to a plane including the first axis and the center and the anchor and the connector is pivotable about the retaining member and anchor so that the second axis is obliquely oriented to the plane.

In another aspect, there is provided a spinal connector system comprising a connector including a saddle portion and an eyelet portion depending from the saddle portion to form a connector body. The saddle portion includes a pair of arms defining a U-shaped passage therebetween for receiving an elongated connecting element therethrough along a first axis and the pair of arms extends away from the eyelet portion along a second axis that is orthogonal to the first axis. The eyelet portion is centered on the second axis between the pair of arms. The eyelet portion further includes a receptacle housing a retaining member therein where the retaining member includes a through-bore extending therethrough along a third axis that is generally orthogonally oriented to the first axis and to the second axis. The system also includes an elongated anchor including a shaft positioned through the through-bore along the third axis. The anchor and the retaining member include a first orientation where the third axis is orthogonal to the first axis and to the second axis and the saddle portion of the connector is pivotable about the retaining member and anchor so that the third axis is obliquely oriented to the at least one of the first axis and the second axis.

In another aspect, a spinal surgical system includes an elongated connecting element positionable along a spinal column between two or more vertebrae of a spinal column segment. The system includes a connector with a saddle portion and an eyelet portion depending from the saddle portion to form a monolithic connector body. The saddle portion defines a passage with the elongated connecting element in the passage along a first axis. The eyelet portion includes a receptacle housing a retaining member therein with the retaining member including a through-bore extending therethrough along a second axis and a center through which the second axis extends. The system also includes an elongated anchor engageable to at least one of the vertebrae. The anchor includes a shaft positioned through the through-bore along the second axis. The retaining member is pivotable in the receptacle prior to engagement of the connector to the connecting element so that when the anchor is positioned through the retaining member the connector is movable relative to any one of a plurality of orientations to the anchor and is then securable in a selected one of these orientations by engagement of the connecting element to the connector.

Also provided are methods for employing systems and techniques for securing a connecting element along the spinal column with an anchor via a connector. The system and method include pivotally coupling the connector to an elongated shaft of the anchor to allow the connector to move relative to the anchor and then securing the connector and anchor in a fixed position relative to one another by securing the connecting element to the connector.

These and other aspects are discussed further below.

BRIEF DESCRIPTION OF THE FIGURES

FIG. 1 is a perspective view of a connector and anchor.

FIG. 2 is a perspective view of a retaining member of the connector of FIG. 1.

FIG. 3 is a partial section view along line 3-3 of FIG. 1 and further showing a connecting element and engaging member.

FIG. 4 is a partial section view along line 4-4 of FIG. 1.

DESCRIPTION OF THE ILLUSTRATED EMBODIMENTS

Figure 5A:
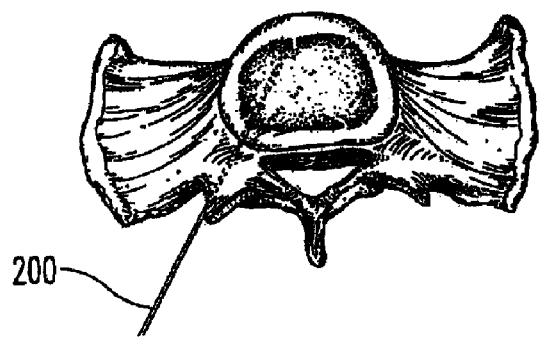
FIGS. 5A-5J show various steps of a surgical procedure for implanting the connector and anchor of FIG. 1 at an ilio-sacral location.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

A system and method for anchoring a connector to a bony portion of a spinal column is provided. In one embodiment, the anchor is an ilio-sacral screw that anchors the connector to the sacrum. The connector is configured to receive an elongate connecting element that is engaged to the sacrum with the connector. The connecting element can also be engaged to one or more additional vertebrae along the spinal column with suitable screws, hooks, transverse connectors, staples, or other anchoring device suitable for the same. The connector includes an eyelet portion that houses a retaining member through which the anchor extends. The retaining member allows movement of the connector relative to the anchor prior to securing the connecting element to the connector. When the connecting element is secured to the connector, the connecting element compresses the retaining member about the anchor through the connector to fix the connector relative to the anchor.

FIG. 1 shows a perspective view of one embodiment connector system 10. Connector system 10 includes an anchor 12 and a connector 30. Anchor 12 includes an elongated shaft 14 that extends along a longitudinal axis 22. Shaft 14 is configured to engage the bony tissue of, for example, the sacrum or vertebral body when implanted. In the illustrated embodiment, shaft 14 includes an outer thread profile 16 to secure shaft 14 to the bony tissue. Thread profile 16 can be configured for insertion in a drilled and tapped bore in the bony tissue. Other embodiments contemplate that thread profile 16 is self-tapping. In yet other embodiments, shaft 14 and thread profile 16 are configured to be self-drilling and self-tapping. Anchor 12 also includes a proximal head 18 at a proximal end of shaft 14. Head 18 is enlarged relative to shaft and includes an internal tool recess or other suitable configuration to receive or engage a driving instrument. Head 18 includes a flat proximally oriented surface to minimize tissue and skin irritation, and to also increase contact with the bone. Rounded proximal surfaces on head 18 are also contemplated. Anchor 12 also includes a longitudinal lumen 20 extending along longitudinal axis 22. Lumen 20 provides a cannulated anchor 12 with lumen 20 that opens at head 18 and at a distal tip 24 of shaft 14. In other embodiments, shaft 14 may include one or more fenestrations or openings to allow delivery of bone growth material to the bony tissue surrounding shaft 14. Other embodiments contemplate a non-cannulated anchor.

Connector 30 includes a saddle portion 32 with a passage 38 to receive a connecting element and an eyelet portion 34 to receive anchor 12. Saddle portion 32 and eyelet portion 34 are formed integrally with one another to provide a monolithic structure. Eyelet portion 34 includes an inner surface 51 that defines a receptacle 50 that houses a retaining member 70 therein. Inner surface 51 extends between and opens at opposite end surfaces 58, 59 of eyelet portion 34. Receptacle 50 extends along receptacle axis 35 between end surfaces 58, 59. Connector 30 further includes a hole 40 in the bottom of saddle portion 32 thereof that opens into and provides communication between passage 38 and receptacle 50.

Retaining member 70 is shown in isolation in FIG. 2. Retaining member 70 includes a circular outer wall 72 that forms a ring-shaped body about a center 71. Receptacle axis 35 extends through center 71 when ring 70 is in receptacle 50. Wall 72 extends between opposite end surfaces 74, 76. Outer wall 72 includes an inner surface 78 that extends around and defines a through-bore 80 centered around center 71. Through-bore 80 extends between and opens at opposite end surfaces 74, 76. Inner surface 78 is smooth and linear between end surfaces 74, 76 in the illustrated embodiment. Other embodiments contemplate that inner surface 78 includes one or more surface interruptions, such as threads, grooves, pits or indentations, and can also be non-linear between end surfaces 74, 76. Outer wall 72 includes an outer surface 82 extending therearound that is linear or straight between end surfaces 74, 76 to form a cylinder.

As shown in FIG. 3, retaining member 70 is housed in receptacle 50 of eyelet portion 34. Through-bore 80 is oriented to align center 71 with longitudinal axis 22 of anchor 12 and receptacle axis 35 when anchor 12 is positioned through retaining member 70. Receptacle 50 includes inner surface 51 extending therearound that is configured to maintain retaining member 70 in eyelet portion 34 while allowing retaining member 70 to pivot and rotate relative to eyelet portion 34. In the illustrated embodiment, inner surface 51 include a central concave portion 52 that is shaped to have contact with outer surface 82 and/or end surfaces 74, 76 of retaining member 70 to maintain retaining member 70 therein. Hole 40 is located at central portion 52 and retaining member 40 is aligned with hole 40 in its axially aligned and pivoted orientations in receptacle 50. Inner surface 51 also includes outwardly flared portions 54, 56 extending from opposite sides of central portion 52 to the respective end surface 58, 59 of eyelet portion 34. Flared portions 54, 56 are configured to flare outwardly so that receptacle 50 widens from central portion 52 to the respective adjacent end surface 58, 59 to accommodate pivoting of anchor 12 in eyelet portion 34.

Eyelet portion 34 further includes an outer surface 39 that extends therearound between end surfaces 34, 36 in the direction along receptacle axis 35. Outer surface 39 is convexly curved between opposite sides of saddle portion 32 located along passage axis 60. Outer surface 39 transitions on each of the opposite sides to the respective adjacent ends of arms 36a, 36b along passage axis 60 and the bottom surface of passage 38 between arms 36a, 36b.

Saddle portion 32 includes a pair of upstanding arms 36a, 36b that extend along a longitudinal axis 31 to an upper opening 37 therebetween. Arms 36a, 36b also define a passage 38 therebetween that is oriented orthogonally to longitudinal axis 31. Passage 38 extends along a passage axis 60 and opens at the opposite ends of arms 36a, 36b. Passage 38 is sized and configured to receive connecting element 100 therein along passage axis 60, such as shown in FIG. 3. Arms 36a, 36b also include internal thread profiles 44a, 44b, respectively, that engage engaging member 102 in, around or adjacent to upper opening 37. Engaging member 102 can be a set screw as shown, or a cap, plug or other threaded or non-threaded device that engages saddle portion 32 internally of arms 36a, 36b, externally of arms 36a, 36b, or both internally and externally, to secure connecting element 100 in passage 38. Arms 36a, 36b can be non-threaded and/or include any suitable configuration to allow securement of engaging member 102 thereto. Arms 36a, 36b may also include recesses 42a, 42b, respectively, that can be engaged by a tool or instrument to facilitate handling and manipulation of connector 30.

Retaining member 70 can be viewed through hole 40 to provide the surgeon with a visual indication that retaining member is properly located in receptacle 50 during the surgical procedure prior to placement of connecting element 100 in passage 38. Furthermore, when connecting element 100 is secured in saddle portion 32 against the bottom surface of saddle portion 32, connecting element 100 contacts retaining member 70 through hole 40 which in turn compresses against anchor 12. This fixes anchor 12 in position in eyelet portion 34 and also fixes the position of anchor 12, retaining member 70 and connector 30 relative to connecting element 100. Hole 40 is sized to maintain sufficient surface area of saddle portion 32 against which connecting element 100 is secured to prevent connecting element 100 from slipping in saddle portion 32 when secured therein. Other embodiments contemplate that hole 40 is not provided.

Anchor 12 and retaining member 70 are sized relative to one another to permit shaft 14 to pass through through-bore 80 when retaining member 70 is positioned in receptacle 50, as shown in FIGS. 1 and 3-4. Anchor 12 and retaining member 70 include a non-pivoted orientation, as indicated by longitudinal axis 22, where longitudinal axis 22 is aligned with receptacle axis 35 and orthogonal to passage axis 60 of passage 38 and longitudinal axis 31 of saddle portion 32. In one embodiment, longitudinal axis 22 is orthogonal to a plane containing passage axis 60 and center 71 of retaining member 70. It is further contemplate that the inter-relationship between inner surface 51 and retaining member 70 permits connector 30 and eyelet portion 34 to pivot and rotate about retaining member 70 so that longitudinal axis 22 is obliquely oriented to the plane containing passage axis 60 and center 71 of retaining member 70, as indicated by longitudinal axis 22' in FIGS. 3-4. This pivoted orientation also positions anchor 12 in an oblique orientation to receptacle axis 35. Furthermore, in the pivoted orientation, longitudinal axis 22' of anchor 20 is obliquely oriented to at least one of longitudinal axis 31 and passage axis 60. The pivoting of eyelet portion 34 about retaining member 70 and anchor 12 allows for angular adjustment capabilities between connector 30 and anchor 12 during implantation prior to securement of connecting element 100 to connector 30. When connecting element 100 is secured to connector 30, connecting element 100 contacts retaining member 70 directly or by pressing saddle portion 32 against retaining member 70. This compresses retaining member 70 and fixes it in position in eyelet portion 34 and also secures retaining member 70 against anchor 12 to fix anchor 12 relative to connector 30.

This angular adjustment capability provides an adjustment angle A between the orthogonal orientation indicated by longitudinal axis 22 and receptacle axis 35 and the oblique orientation indicated by longitudinal axis 22'. In one embodiment, angle A is about 15 degrees. Other embodiments contemplate other angles for the angular adjustment capability. It is also contemplated that the angular adjustment is universal or in all directions from longitudinal axis 22 such that anchor 12 is movable in any direction from receptacle axis 35 and alignable along any axis contained within a cone having a perimeter defined by longitudinal axis 22', as shown in FIG. 1.

Connector 30 further includes a compact configuration that allows it to be secured to the sacrum while minimizing its intrusion into adjacent tissue. Eyelet portion 34 is centered on longitudinal axis 31 between arms 36a, 36b. Furthermore, the outer surface 39 of eyelet portion 34 does not protrude in the direction of passage axis 60 from beyond the ends of arms 36a, 36b located along passage axis 60. Connecting element 100 may be conveniently top-loaded into passage 38 through upper opening 37 for positioning in passage 38 between arms 36a, 36b. Connector 30 can be pivoted relative to anchor 12 and retaining member 70 and or rotated about retaining member 70 to position opening 37 in a location and orientation to receive connecting element 100 into passage 38.

Figure 5B:
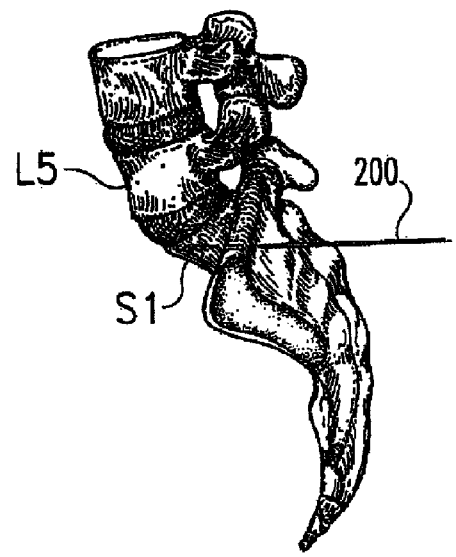
Figure 5C:
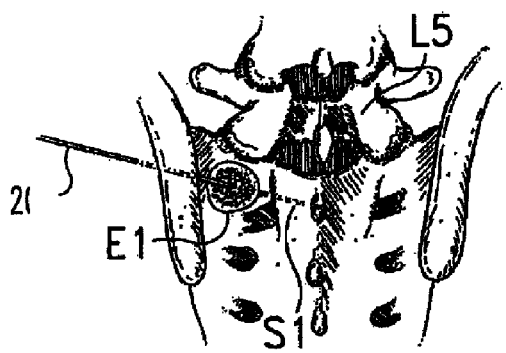
Figure 5D:
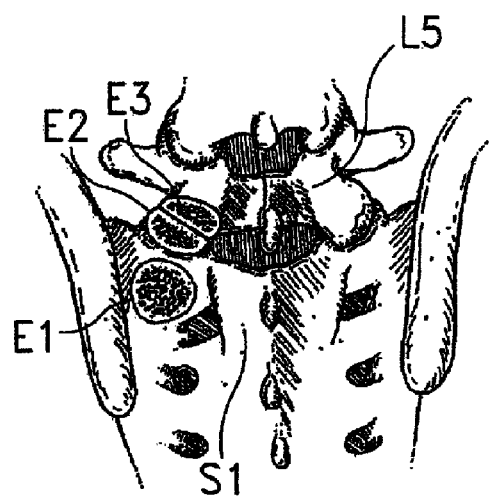

Referring to FIGS. 5A-5J, an example of a surgical procedure for implanting connector system 10 will be described. FIG. 5A is a view in the axial plane and looking caudally at the sacrum and ilium, FIG. 5B is an elevation view of the sacrum and lower lumbar vertebrae looking medially from the side, and FIG. 5C is an elevation view of the posterior elements looking in the anterior direction. In FIGS. 5A-5C a guidewire 200 is positioned so that the entry point for anchor 12 is inferior and lateral to the facet joint of the L5 and S1 vertebrae. The leading end of guidewire 200 is angled toward the sacral promontory as shown in FIG. 5B, and also angled medially from the entry point into S1 as shown in FIG. 5A. The bone around the entry point location E1 is removed or otherwise shaped around guidewire 200 to facilitate placement of connector 30 thereagainst as shown in FIGS. 5C and 5D. Bone from the S1 and L5 facet joint can also be removed at locations E2 and E3 to facilitate placement of the connecting element from the L5 vertebrae to connector 30 as shown in FIG. 5D. If necessary, guidewire 200 can be removed to facilitate removal of the bone.

Figure 5E:
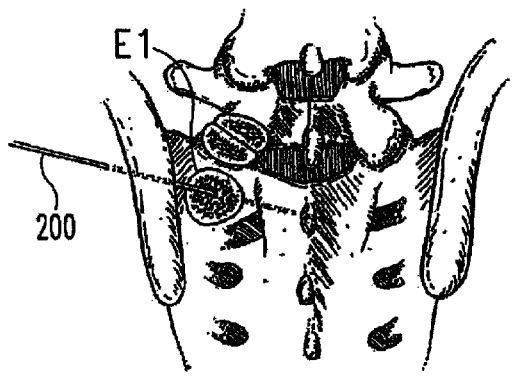
Figure 5F:
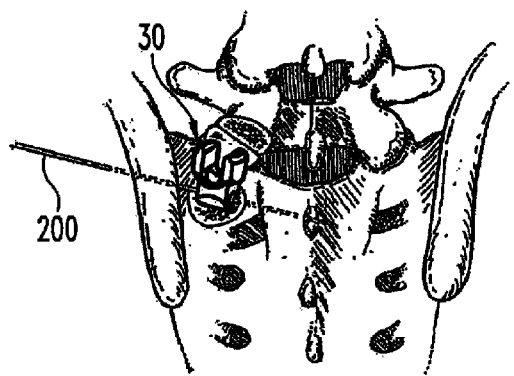
Figure 5G:
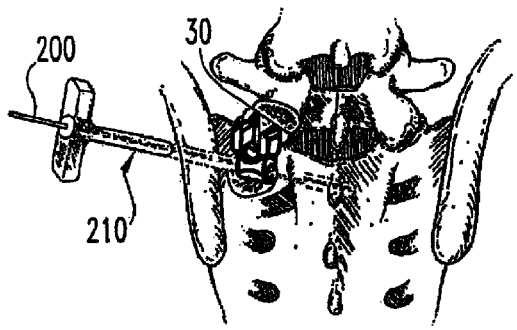
Figure 5H:
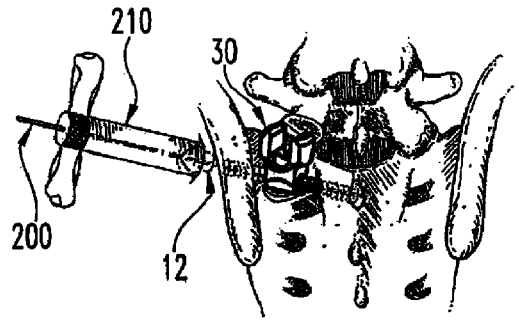
Figure 5I:
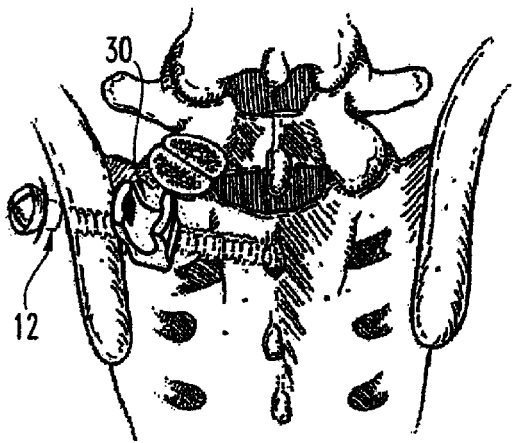
Figure 5J:
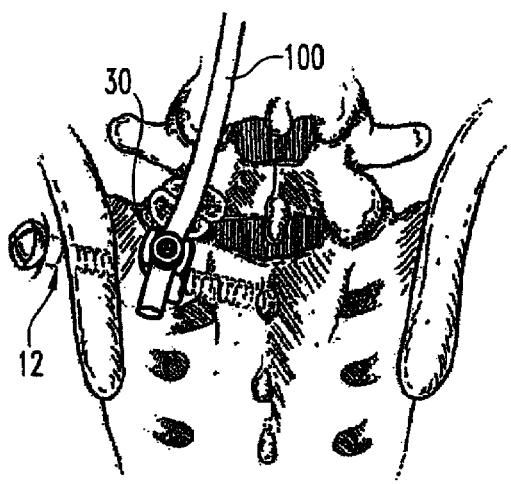

In FIG. 5E guidewire 200 is repositioned, if necessary, into the entry point into S1, and as shown in FIG. 5F connector 30 is advanced along guidewire 200 to location E1. Eyelet portion 34 is positioned around guidewire 200 to guide eyelet portion 34 to the entry location for anchor 12. In FIG. 5G a drill 210 is placed over guidewire 200 and guided to entry location E1. Drill 210 extends through eyelet portion 34 to drill a bore along the path defined by guidewire 200 to receive anchor 12. In FIG. 5H drill 210 is removed and anchor 12 is secured to a driver 220. Anchor 12 and driver 220 are guided along guidewire 200 through eyelet portion 34 and into the pre-drilled bore formed by drill 210. As shown in FIG. 5I, driver 220 is removed and connector 30 is secured to sacrum S1 with anchor 12. Anchor 12 is driven into the bone through eyelet portion 34 of connector 30 until it extends proximally from connector 30 along the ilium. In FIG. 5J connecting element 100 is positioned in saddle portion 34 of connector 30 and secured therein with engaging member 102.

Prior to securement of connecting element 100 in saddle portion 32, the pivotal and rotational relationship of connector 30 relative to anchor 12 allows relative movement between connector 20 and connecting element 100 to accommodate insertion of connecting element 100 into saddle portion 32 while connector 30 is secured to the spinal column. When connecting element 100 is secured to connector 30, micromotions and other movement of the pelvic region do not result in loosening of anchor 12 since anchor 12 is fixed in position relative to connecting element 100 by connecting element 100 compressing retaining member 70 about anchor 12 in eyelet portion 34.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A spinal connector system, comprising:
 a connector including a saddle portion and an eyelet portion depending from said saddle portion to form a monolithic connector body, said saddle portion defining a passage for receiving an elongated connecting element therethrough along a first axis and said eyelet portion including a receptacle, said receptacle housing a retaining member therein, said retaining member including a through-bore extending therethrough along a second axis and a center through which said second axis extends; and
 an elongated anchor including a shaft positioned through said through-bore along said second axis, wherein said anchor and said retaining member include a first orientation in said eyelet portion wherein said second axis is orthogonal to a plane including said first axis and said center and said connector is pivotable about said retaining member in said receptacle so that said second axis is obliquely oriented to said plane, wherein said shaft of said elongated anchor defines a central lumen extending between an opening at a proximal end of said shaft and an opposite distal end of said shaft.

2. The system of claim 1, further comprising an elongated connecting element in said passage of said saddle portion.

3. The system of claim 2, further comprising an engaging member engaged to said saddle portion to secure said connecting element in said passage.

4. The system of claim 3, wherein said connector includes a hole extending between and opening into said passage and said receptacle and said connecting element contacts said retaining member through said hole and compresses said retaining member about said anchor to fix said anchor and said connecting member relative to said connecting element.

5. The system of claim 1, wherein said saddle portion includes a pair of arms extending away from said eyelet portion on opposite sides of said passage along a third axis, said pair of arms further defining an upper opening therebetween on said third axis, wherein said third axis is orthogonal to each of said first axis and said second axis.

6. The system of claim 1, wherein said eyelet portion includes an inner surface defining said receptacle, said inner surface extending between opposite sides of said eyelet portion and said receptacle opens at said opposite sides, wherein said inner surface includes a concave central portion extending around said receptacle between said opposite sides and opposite outwardly flared surface portions extending from said central portion to respective ones of said opposite sides.

7. The system of claim 1, wherein said through-bore opens at opposite end surfaces of said retaining member and said retaining member includes a linear outer surface extending between said opposite end surfaces.

8. The system of claim 1, wherein said connector is pivotable about said retaining member so that said second axis is movable to an oblique orientation relative to said plane in every direction from said first orientation.

9. The system of claim 1, wherein said shaft of said anchor includes an outer thread profile, and an enlarged head at said proximal end of said shaft with a flat proximal surface.

10. A spinal connector system, comprising:
a connector including a saddle portion and an eyelet portion depending from said saddle portion to form a connector body, said saddle portion including a pair of arms defining a U-shaped passage therebetween for receiving an elongated connecting element therethrough along a first axis and said pair of arms extend away from said eyelet portion along a second axis that is orthogonal to said first axis, wherein said eyelet portion is centered on said second axis between said pair of arms, said eyelet portion further including a receptacle housing a retaining member therein, said retaining member including a through-bore extending therethrough along a third axis that is generally orthogonally oriented to said first axis and to said second axis; and
an elongated anchor including a shaft positioned through said through-bore along said third axis, wherein said anchor and said retaining member include a first orientation wherein said third axis is orthogonal to each of said first axis and said second axis and said connector is pivotable about each of said retaining member and said anchor so that said third axis is obliquely oriented to said at least one of said first axis and said second axis, wherein said shaft of said elongated anchor defines a central lumen extending between an opening at a proximal end of said shaft and an opposite distal end of said shaft.

11. The system of claim 10, wherein said through-bore opens at opposite end surfaces of said retaining member and said retaining member includes a linear outer surface extending between said opposite end surfaces.

12. The system of claim 11, wherein:
said eyelet portion includes an inner surface defining said receptacle, said inner surface extending between opposite sides of said eyelet portion and said receptacle opens at said opposite sides;
said inner surface includes a concave central portion extending around said receptacle between said opposite sides and opposite outwardly flared surface portions extending from said central portion to respective ones of said opposite sides; and
said retaining member resides in said concave central portion of said inner surface of said eyelet portion.

13. The system of claim 10, wherein said connector body is monolithic and includes a hole extending between said passage and said receptacle and said retaining member is aligned with said hole.

14. The system of claim 10, wherein connector is pivotable relative to each of said anchor and said retaining member in said receptacle so that said third axis is obliquely oriented to each of said first axis and said second axis.

15. A spinal surgical system, comprising:
an elongated connecting element positionable along a spinal column between two or more vertebrae of a spinal column segment;
a connector including a saddle portion and an eyelet portion depending from said saddle portion to form a monolithic connector body, said saddle portion defining a passage with said elongated connecting element in said passage along a first axis, said eyelet portion including a receptacle housing a retaining member therein, said retaining member including a through-bore extending therethrough along a second axis and a center through which said second axis extends; and
an elongated anchor engageable to at least one of the vertebrae, said anchor including a shaft positioned through said through-bore along said second axis, wherein said retaining member is pivotable in said receptacle so that when said anchor is positioned through said retaining member in said saddle portion said connector pivots relative to said retaining member and when said connecting element is secured in said saddle portion said connecting element compresses said retaining member about said anchor to fix said anchor and said retaining member in position relative to said connector, wherein said shaft of said elongated anchor defines a central lumen extending between an opening at a proximal end of said shaft and an opposite distal end of said shaft.

16. The system of claim 15, wherein said anchor and said retaining member are positionable in a first orientation wherein said second axis is orthogonal to a plane defined by said first axis and said center of said retaining member and said connector is pivotable about said retaining member so that said second axis is obliquely oriented to said plane.

17. The system of claim 16, wherein said connector is pivotable about said retaining member so that said second axis is movable to an oblique orientation relative to said plane in every direction from said first orientation.

18. The system of claim 15, wherein said saddle portion includes a pair of arms on opposite sides of said passage extending away from said eyelet portion along a third axis that is orthogonal to said first axis and said second axis, and said eyelet portion is centered between said pair of arms on said third axis.

19. The system of claim 15, wherein said eyelet portion includes an inner surface defining said receptacle, said inner surface extending between opposite sides of said eyelet portion and said receptacle opens at said opposite sides, wherein said inner surface includes a concave central portion extending around said receptacle between said opposite sides and opposite outwardly flared surface portions extending from said central portion to respective ones of said opposite sides.

20. The system of claim 19, wherein:
said through-bore opens at opposite end surfaces of said retaining member;
said retaining member includes a linear outer surface extending between said opposite end surfaces, said linear outer surface residing within said concave surface of said central portion of said inner surface;
said connector includes a hole between said passage and said concave surface of said central portion of said receptacle;
said retaining member is aligned with said hole; and
said connecting element contacts said retaining member through said hole when said connecting element is secured to said saddle portion.

* * * * *